United States Patent
Vonderwalde

(10) Patent No.: US 8,882,822 B2
(45) Date of Patent: *Nov. 11, 2014

(54) NON-THROMBOGENIC STENT JACKET

(75) Inventor: Carlos Vonderwalde, Richmond (CA)

(73) Assignee: Design & Performance-Cyprus Limited, Nicosia (CY)

( * ) Notice: Subject to any disclaimer, the term of this patent is extended or adjusted under 35 U.S.C. 154(b) by 1769 days.

This patent is subject to a terminal disclaimer.

(21) Appl. No.: 11/181,978

(22) Filed: Jul. 15, 2005

(65) Prior Publication Data

US 2005/0251244 A1 Nov. 10, 2005

Related U.S. Application Data

(63) Continuation-in-part of application No. 09/716,038, filed on Nov. 17, 2000, now abandoned, which is a continuation of application No. 09/156,034, filed on Sep. 17, 1998, now Pat. No. 6,254,627, which is a continuation-in-part of application No. 09/053,200, filed on Apr. 1, 1998, now abandoned, which is a continuation-in-part of application No. 09/035,114, filed on Mar. 4, 1998, now abandoned, which is a continuation-in-part of application No. 09/005,972, filed on Jan. 12, 1998, now abandoned, which is a continuation-in-part of application No. 08/935,784, filed on Sep. 23, 1997, now Pat. No. 6,468,300.

(51) Int. Cl.
*A61F 2/06* (2013.01)
*A61F 2/90* (2013.01)
*A61F 2/07* (2013.01)

(52) U.S. Cl.
CPC ... *A61F 2/07* (2013.01); *A61F 2/90* (2013.01); *A61F 2002/075* (2013.01); *Y10S 623/901* (2013.01)

USPC ....... 623/1.13; 623/1.42; 623/23.72; 623/901

(58) Field of Classification Search
USPC .......... 623/1.13, 1.41–1.44, 1.47, 23.7, 23.72
See application file for complete search history.

(56) References Cited

U.S. PATENT DOCUMENTS

| 4,400,833 A | 8/1983 | Kurland |
| 4,470,157 A | 9/1984 | Love |
| 4,477,930 A | 10/1984 | Totten et al. |
| 4,502,159 A | 3/1985 | Woodroof et al. |

(Continued)

FOREIGN PATENT DOCUMENTS

| EP | 0804907 | 5/1997 |
| EP | 0839506 | 6/1998 |

(Continued)

OTHER PUBLICATIONS

Burbelko et al "Stent-Graft Placement for Wide-Neck Aneurysm of the Vertebrobasilar Junction"—American Journal of neuroradiology 25:608-610, Apr. 2004.

*Primary Examiner* — Paul Prebilic
(74) *Attorney, Agent, or Firm* — Greenberg Traurig, LLP

(57) ABSTRACT

Disclosed is the use of serous tissue, such as pericardium, as a component of intracorporeal implants. Particularly, disclosed is a jacketed stent assembly comprising an expandable stent provided with a jacket of processed serous tissue which, in some embodiments, is impregnated with a therapeutic or diagnostic agent. In a preferred embodiment, the jacket of the expandable stent is formed of pericardial tissue, preferably bovine or porcine pericardial tissue.

9 Claims, 3 Drawing Sheets

(56) References Cited

U.S. PATENT DOCUMENTS

| | | | |
|---|---|---|---|
| 4,801,299 A | 1/1989 | Brendel et al. | |
| 4,902,508 A | 2/1990 | Badylak et al. | |
| 4,994,071 A | 2/1991 | MacGregor | |
| 5,163,955 A | 11/1992 | Love et al. | |
| 5,383,928 A | 1/1995 | Scott et al. | |
| 5,443,497 A | 8/1995 | Venbrux | |
| 5,456,712 A | 10/1995 | Maginot | |
| 5,489,297 A * | 2/1996 | Duran | 623/2.13 |
| 5,489,298 A | 2/1996 | Love et al. | |
| 5,512,291 A | 4/1996 | Li | |
| 5,549,663 A | 8/1996 | Cottone | |
| 5,556,414 A | 9/1996 | Turi | |
| 5,571,173 A | 11/1996 | Parodi | |
| 5,575,818 A | 11/1996 | Pinchuk | |
| 5,584,876 A | 12/1996 | Bruchman et al. | |
| 5,599,307 A | 2/1997 | Bacher et al. | |
| 5,617,878 A | 4/1997 | Taheri | |
| 5,628,786 A | 5/1997 | Banas et al. | |
| 5,641,373 A | 6/1997 | Shannon et al. | |
| 5,653,743 A | 8/1997 | Martin | |
| 5,653,747 A | 8/1997 | Dereume | |
| 5,667,523 A | 9/1997 | Bynon et al. | |
| 5,669,924 A | 9/1997 | Shaknovich | |
| 5,674,298 A | 10/1997 | Levy et al. | |
| 5,676,697 A | 10/1997 | McDonald | |
| 5,693,085 A | 12/1997 | Buirge et al. | |
| 5,707,385 A | 1/1998 | Williams | |
| 5,723,004 A | 3/1998 | Dereume et al. | |
| 5,741,326 A | 4/1998 | Solovay | |
| 5,755,778 A | 5/1998 | Kleshinski | |
| 5,782,914 A | 7/1998 | Schankereli | |
| 5,865,723 A | 2/1999 | Love | |
| 5,906,640 A | 5/1999 | Penn et al. | |
| 5,916,266 A * | 6/1999 | Yui et al. | 424/423 |
| 5,934,283 A | 8/1999 | Willem et al. | |
| 5,961,548 A | 10/1999 | Shmulewitz | |
| 5,972,017 A | 10/1999 | Berg et al. | |
| 5,980,565 A | 11/1999 | Jayaraman | |
| 5,984,955 A | 11/1999 | Wisselink | |
| 5,997,573 A | 12/1999 | Quijano et al. | |
| 6,017,363 A | 1/2000 | Hojeibane | |
| 6,090,133 A | 7/2000 | Richter et al. | |
| 6,117,166 A | 9/2000 | Winston et al. | |
| 6,183,509 B1 | 2/2001 | Dibie | |
| 6,210,429 B1 | 4/2001 | Vardi et al. | |
| 6,254,627 B1 * | 7/2001 | Freidberg | 623/1.11 |
| 6,302,908 B1 | 10/2001 | Parodi | |
| 6,378,221 B1 | 4/2002 | Ekholm et al. | |
| 6,432,712 B1 * | 8/2002 | Wolfinbarger, Jr. | 435/395 |
| 6,468,300 B1 * | 10/2002 | Freidberg | 623/1.13 |
| 6,468,313 B1 | 10/2002 | Claeson et al. | |
| 6,699,277 B1 * | 3/2004 | Freidberg et al. | 623/1.13 |
| 7,108,717 B2 * | 9/2006 | Freidberg | 623/1.41 |
| 7,559,953 B2 * | 7/2009 | Sarac | 623/23.72 |
| 2002/0116047 A1 | 8/2002 | Vardi et al. | |
| 2002/0123789 A1 * | 9/2002 | Francis et al. | 623/1.13 |
| 2003/0018378 A1 * | 1/2003 | Sarac | 623/1.13 |
| 2006/0136047 A1 * | 6/2006 | Obermiller et al. | 623/1.41 |

FOREIGN PATENT DOCUMENTS

| | | |
|---|---|---|
| EP | 0716836 | 4/2001 |
| WO | WO 93/20757 | 10/1993 |
| WO | WO 94/15583 | 7/1994 |
| WO | WO 97/15346 | 1/1997 |
| WO | WO 97/09006 | 3/1997 |
| WO | WO 97/12563 | 4/1997 |
| WO | WO 97/45073 | 4/1997 |
| WO | WO 97/17913 | 5/1997 |
| WO | WO 97/24081 | 7/1997 |
| WO | WO 97/41803 | 11/1997 |
| WO | WO 97/46174 | 12/1997 |
| WO | WO 97/46175 | 12/1997 |
| WO | WO 98/25543 | 6/1998 |

* cited by examiner

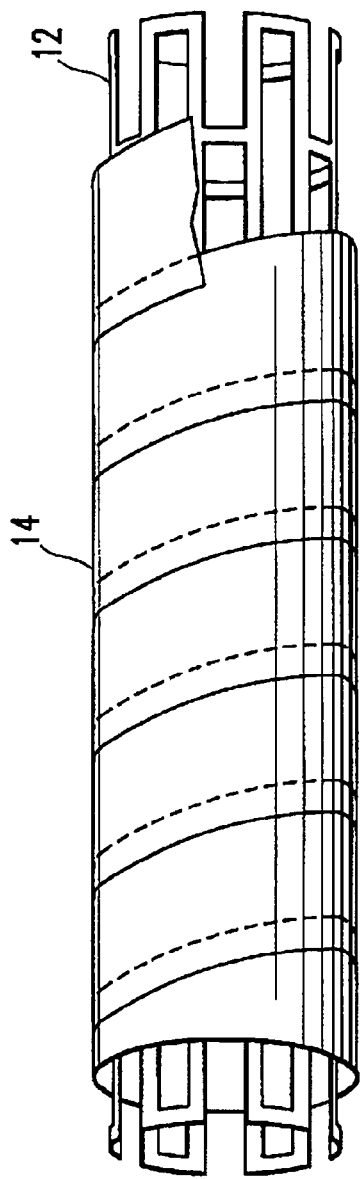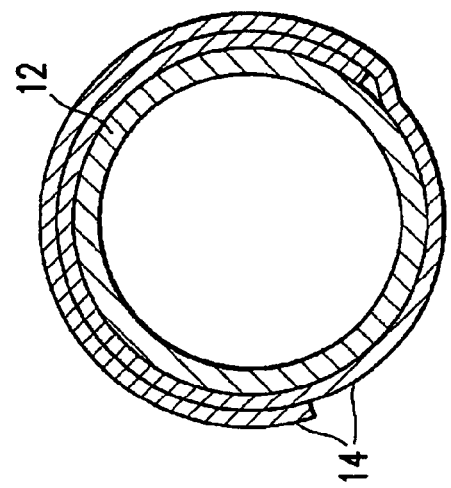

NON-THROMBOGENIC STENT JACKET

RELATED APPLICATIONS

This application is a Continuation-In-Part (CIP) of U.S. application Ser. No. 09/716,038, filed on Nov. 17, 2000, now abandoned, which is Continuation of U.S. application Ser. No. 09/156,034, filed on Sep. 17, 1998, now U.S. Pat. No. 6,254,627, issued on Jul. 3, 2001, which is a Continuation-In-Part (CIP) of U.S. application Ser. No. 09/053,200, filed on Apr. 1, 1998, now abandoned, which is a Continuation-In-Part (CIP) of U.S. application Ser. No. 09/035,114, filed on Mar. 4, 1998, now abandoned, which is a Continuation-In-Part (CIP) of U.S. application Ser. No. 09/005,972, filed on Jan. 12, 1998, now abandoned, which is Continuation-In-Part (CIP) of U.S. application Ser. No. 08/935,784, filed on Sep. 23, 1997, now U.S. Pat. No. 6,468,300, issued on Oct. 22, 2002.

The above Applications are all hereby incorporated by reference.

FIELD AND BACKGROUND OF THE INVENTION

The present invention relates to the field of medicine, and more particularly to the field of intracorporeal devices such as stents. The present invention also relates to the field of expandable intraluminal support devices such as stents and the like.

Typically, stents are expandable, tubular metallic devices that are positioned within a patient's vasculature or other body lumen and expanded in order to support a vessel or body lumen and allow the flow of blood or other body fluids therethrough. Often, the stents are formed from a deformable metal and delivered to a desired intraluminal location using a balloon-type catheter. By advancing the catheter through the body lumen, the stent may be delivered to a desired position. Inflating the balloon then deforms the stent into an expanded configuration, seating it within the artery or other body lumen. Other implementations make use of a self-expanding stent formed from a suitable material such as pseudoelastic material that is delivered in a constricted condition and when released spontaneously expands to an enlarged configuration. In other embodiments, a stent made of shape memory alloy (e.g. NiTi alloy) is inserted into the body lumen in a martensitic phase and transforms to an austenite phase which has an expanded memory when raised to a temperature above the transformation temperature, usually less than 45° C.

Stents are often used in conjunction with an intravascular treatment for obstructive coronary artery disease. For example, ablation, atherectomy, balloon dilation, laser treatment or other procedures are among the method used to widen a stenotic region of a patient's vasculature. However, restenosis occurs in large percentage of percutaneous transluminal coronary angioplasty (PTCA) patients and rates can be even higher with other procedures. The prior art has employed a number of mechanical and pharmacological strategies to reduce the restenosis rate, but none have been particularly effective. Accordingly, stents have been proposed to maintain the patency of a treated vessel and prevent restenosis. Using stents, restenosis rates have fallen to less than 20%.

Restenosis is thought to be a natural healing reaction provoked by injury from the intravascular procedure. The healing process frequently causes thrombosis and may lead to intimal hyperplasia that occludes the vessel. Although helpful in reducing restenosis, stents do not represent a complete solution. The framework of the stent may still allow migration and proliferation of the smooth muscle cells, while the stent itself can be thrombogenic. To address these problems, stents have been covered with DACRON, PTFE and autologous vein and the surface has been seeded with endothelial cells or otherwise treated. Each of these solutions suffer from certain drawbacks, such as not being biocompatible, lacking sufficient mechanical strength, having a surface that is difficult to prepare, lack of ready availability and being thrombogenic.

Antithrombotic drug regimens, in which anticoagulants and thrombolytic agents are administered during and after deployment of the stent, have also been employed to reduce the risk of thrombosis.

In the art it is known to cover stents with jackets made of serous membrane.

Serous membrane is a type of tissue that holds various organs together and include the peritoneum (the serous membrane that lines the cavity of the abdomen of a mammal and is folded inward over the abdominal and pelvic viscera), the pericardium (the conical sac of serous membrane that encloses the heart and the roots of the great blood vessels) and the pleura (the serous membrane that lines each half of the thorax and is folded back over the surface of the lung of the same side). The serous membranes release a lubricating serous fluid allowing the expanding and contracting organs (including the lungs) held within a given serous membrane to slide gently against adjacent parts of the body.

Serous membranes are made of two strata of tissue. The serous stratum or layer of a serous membrane is a very smooth single layer of flattened, nucleated mesothelial cells united at their edges by cement substance. The serous layer is the side that faces towards and contacts the organs. The serous cells secrete the lubricating serous fluid. The serous cells rest on a basement layer or stratum (also called the subserous areolar tissue), a rough, strong fibrous layer that forms a protective sack about the serous layer. Beneath the basement membrane are networks of yellow elastic and white fibers imbedded in ground substance that also contains connective-tissue cells.

The use of serous membranes as a component of intracorporeal implants is known in the art.

In U.S. Pat. No. 4,502,159 is taught a method for preparing a tubular graft from pericardium.

In U.S. Pat. No. 5,782,914 is taught a method for processing animal tissue such as serous membranes for use as a graft material in intracorporeal implants.

In U.S. Pat. No. 5,934,283 is taught the use of tissues, including serous tissues such as pericardium, peritoneum and tunica vaginalis in fashioning a pubovaginal sling.

In U.S. Pat. No. 5,865,723 and in PCT Patent Application No. PCT/US96/20868 published as WO 97/24081 is discussed that vascular prostheses of autologous pericardial membrane fashioned into tubular grafts have been used but have been proven to be ineffective, for example as the pericardial membrane is subject to rupture and structural failure. Therefore in WO 97/24081 is taught a stent assembly comprising pericardial, fascial rectus sheath or venous tissue formed as a jacket over a stent. The tissue is harvested, usually but not necessarily treated in a stabilizing medium, and attached to the outside of the stent by rolling over the stent so that the two edges of the tissue overlap by at least 35° (and preferably are wrapped twice about the stent) so as to obviate the need for sutures.

Due to the overlapping layers of pericardium, stent assemblies jacketed in accordance with the teachings of WO 97/24081 are quite thick, causing a significant reduction in the bore size of a bodily vessel in which deployed, limiting such stent assemblies for deployment only to relatively large bore lumina. Further, the thickness of a stent jacket made in accordance with the teachings of WO 97/24081 reduces the flexibility and consequently maneuverability of such a stent assembly, limiting the locations in which such stents can be deployed.

In PCT Patent Application No. PCT/US96/13907 published as WO 97/09006 is taught a stent assembly comprising a jacket of at least one layer of pericardial tissue (preferably human, bovine or porcine origin) covering at least a portion of the inside or outside surface of a stent. The thickness of the jacket is adjusted by varying the number of layers of pericardium. The disadvantages of such stent assemblies are similar to those of WO 97/24081.

Thus, there is a need for a stent capable of minimizing restenosis while having a consistency similar to the native artery, a non-thrombogenic surface and sufficient mechanical strength as well as being biocompatible and readily available.

It would be highly advantageous to have a material for use as a component in intracorporeal implants such as stents not having at least some of the disadvantages of the prior art.

SUMMARY OF THE INVENTION

The advantages of the teachings of the present invention are clear to one skilled in the art upon perusal of the description herein. The teachings of the present invention provide a processed serous membrane that can be used as a component in intracorporeal implants such as stents having many advantages of the previously-used serous membranes yet is thinner. The fact that the processed serous membrane of the present invention is thin yet sufficiently flexible and strong allows the production of smaller and finer intracorporeal implants than previously known. In the field of stents this is exceptionally important as it allows the deployment of stents in smaller blood vessels, allows the use of smaller deployment catheters, provides a much more flexible covered stent to maneuver inside the cardiovascular network and reduces the bore of a vessel in which deployed to a less significant degree then heretofore known. Further, the unexpected flexibility and strength of the processed serous membrane of the present invention allows the production of stent assemblies including a jacket and a self-expanding stent or of stents that are balloon expandable at low pressures, something that was heretofore difficult if not impossible.

The invention is a stent assembly suitable for maintaining the patency of a bodily lumen, generally comprising an expandable, tubular framework comprising a stent at least in part within a cylinder of biocompatible, non-thrombogenic expandable material such as heterologous tissue.

Preferably, the heterologous tissue comprises bovine pericardium, but other preferred embodiments include porcine pericardium, aortic leaflet and other suitable heterologous tissue. The expandable, tubular framework may be a conventional metallic stent. The stent may be an expandable, tubular framework and may be a conventional self-expanding or balloon expandable stent. The jacket is disposed about either or both of the outer and inner surfaces of the stent. In a preferred embodiment, the jacket is generally cylindrical for corresponding to the tubular framework or the stent.

According to the teachings of the invention, a stent assembly is provided, comprising: a. an expandable stent; and b. functionally associated with the expandable stent, a stent jacket substantially of a thinned serous membrane having a thickness of less than 0.25 mm, wherein the thinned serous membrane comprises a harvested serous membrane that has been thinned by removal of a layer of basement tissue from the harvested serous membrane. In some embodiments, the jacket is fit about the outer surface of the expandable stent. In some embodiments, the jacket is fit on the inner surface of the expandable stent. In some embodiments, the stent assembly further comprises a therapeutic or diagnostic agent releasably contained within the stent jacket. In some embodiments, the thinned serous membrane preferably has a thickness of about 0.05 mm to about 0.20 mm, and most preferably about 0.1 mm to about 0.15 mm. The stent jacket may have a folded or overlapping wrapped configuration when applied to the stent.

According to the teachings of the invention there is also provided a stent assembly, comprising: a. an expandable stent; and b. functionally associated with the expandable stent, a stent jacket essentially consisting of a serous tissue layer substantially devoid of a basement tissue layer and having a thickness of less than 0.25 mm. In some embodiments, the jacket is fit about the outer surface of the expandable stent. In some embodiments, the jacket is fit on the inner surface of the expandable stent. In some embodiments, the stent assembly further comprises a therapeutic or diagnostic agent releasably contained within the stent jacket. In some embodiments, the thinned serous membrane preferably has a thickness of about 0.05 mm to about 0.20 mm, and most preferably about 0.1 mm to about 0.15 mm. The stent jacket may have a folded or overlapping wrapped configuration when applied to the stent.

According to the teachings of the invention there is also provided a method of producing a stent assembly, comprising: a. providing a sheet of serous membrane including a serous tissue stratum and a basement tissue stratum; b thinning the sheet of serous membrane by removing a layer of the basement tissue stratum thereby making a sheet of thinned serous membrane having a thickness of less than 0.25 mm; c. associating the sheet of thinned serous membrane with an expandable stent, thereby producing the stent assembly. In some embodiments, the thinning is of the entire basement tissue stratum. In some embodiments, the thinning is effected by at least one method selected from the group consisting of peeling and shaving. In some embodiments, the associating includes wrapping the sheet about the expandable stent. In some embodiments, the associating includes fitting the processed serous membrane on the inner surface of the expandable stent. In some embodiments, the method further comprises: d. impregnating the sheet of serous membrane with a liquid containing a therapeutic or diagnostic agent.

This invention is also directed to a method for maintaining the patency of a bodily lumen comprising the steps of mounting a stent assembly of a tubular expandable, metallic framework forming the stent coaxially disposed within a cylinder of biocompatible, non-thrombogenic expandable material such as heterologous tissue on an expandable member on the distal extremity of a catheter; advancing the catheter through the bodily lumen until the stent assembly is positioned at a desired location; expanding the stent assembly by expanding the expandable member onto which the stent assembly is mounted to anchor it within the bodily lumen; contracting the expandable member, e.g. deflating the balloon, and withdrawing the catheter. The expanded cylinder of biocompatible, non-thrombogenic expandable material such as heterologous tissue should extend over a substantial portion, preferably all, of the stenotic region in which it is disposed.

This invention is also directed to a method for maintaining the patency of a bodily lumen generally comprising providing a delivery catheter having an expandable member on the distal extremity thereof, mounting the stent assembly, including a tubular stent with a jacket of biocompatible, non-thrombogenic expandable material such as heterologous tissue disposed about at least part of the stent, on the expandable member on the distal extremity of the delivery catheter. The catheter is advanced through the body lumen within the patient until the distal extremity of the catheter having the stent assembly is positioned at a desired location therein. The stent assembly is expanded by expanding the expandable member onto which the stent assembly is mounted to anchor the stent assembly within the body lumen. Once the stent assembly is effectively positioned within the body lumen, the expanded expandable member may be contracted, e.g. by deflating the balloon, and then the delivery catheter may be withdrawn.

A presently preferred embodiment of the invention is directed to a stent assembly suitable for expansion within a body lumen and delivery of a therapeutic or diagnostic agent therein, generally comprising an expandable stent and an expandable, biocompatible, non-thrombogenic jacket such as heterologous tissue, which contains the therapeutic or diagnostic agent and which is disposed about the expandable stent. The jacket releasably contains at least one therapeutic or diagnostic agent.

A wide variety of therapeutic or diagnostic agents for a variety of indications can be used, including angiogenesis agents, chemotherapeutic agents, antibiotic/antirejection agents and antithrombotic agents. The term "antithrombotic agents" is meant to include various agents for reducing the risk of thrombosis, including anticoagulants such as heparin, thrombolytic agents such as urokinase, streptokinase, tissue plasminogen activator (Actilyse®), monoclonal antibodies such as Abciximab (ReoPro), fibrinolytic agents, and the like. Angiogenesis agents that stimulate the growth of neo-vessels include agents such as basic Fibroblast Growth Factor (bFGF) and Vascular Endothelial Growth Factor (VEGF). Chemotherapeutic agents include agents such as Paclitaxel (Taxol®). Antibiotic/anti-rejection agents include agents such as Sirolimus (Rapamune®).

In a presently preferred embodiment, the jacket is impregnated with a liquid containing the therapeutic or diagnostic agent. For example, a jacket formed from heterologous tissue which is submerged in a solution of the therapeutic agent will absorb the solution. A variety of suitable methods of applying the agent to the jacket may be used, including using electrodeposition, heat and pressure. Thereafter, the stent assembly can be positioned at a desired site within the patient's body lumen, where the jacket will release the therapeutic agent. The jacket on the stent assembly may be impregnated just before use, or alternatively, stored in the therapeutic or diagnostic agent so that the stent assembly is preimpregnated.

The invention is also directed to a method for delivery of a therapeutic or diagnostic agent within a body lumen. The stent assembly including a tubular stent with a jacket of biocompatible, non-thrombogenic expandable material, such as heterologous tissue, containing a therapeutic or diagnostic agent is positioned within the body lumen as outlined above. With the stent assembly positioned at a desired location, the therapeutic or diagnostic agent is released from the jacket into the body lumen and thereby delivered at and around the location of the stent assembly within the body lumen.

The expanded jacket of biocompatible, non-thrombogenic expandable material such as heterologous tissue should extend over a substantial portion, preferably all, of the stenotic region in which it is disposed in order to minimize the restenosis.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 7 is a perspective view, partially broken away, of one embodiment of the stent assembly having a biocompatible non-thrombogenic jacket comprising an overlapping ribbon; and FIG. 8 is transverse cross sectional view of one embodiment of the stent assembly prior to being expanded, having a biocompatible non-thrombogenic jacket in an overlapping wrapped configuration.

PREFERRED EMBODIMENTS OF THE INVENTION

Figure 1:
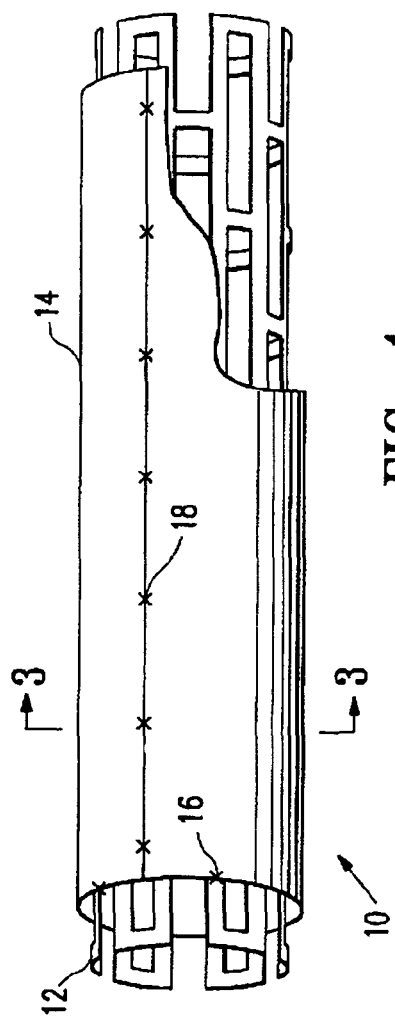
FIG. 1 is a perspective view, partially in section, of a stent assembly of the invention showing the tubular, expandable, metallic stent positioned coaxially within a cylindrical exterior jacket of heterologous tissue.

The principles and uses of the teachings of the present invention may be better understood with reference to the accompanying description, figures and examples. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Generally, the nomenclature used herein and the laboratory procedures utilized in the present invention include techniques from the fields of biology, chemistry, engineering and physics. Such techniques are thoroughly explained in the literature. Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention. All publications, patent applications, patents and other references mentioned are incorporated by reference in their entirety as if fully set forth herein. In case of conflict, the specification herein, including definitions, will control.

As used in the claims, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

As used in the claims, the phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Herein the terms "framework" and "stent" are often used interchangeably, and refer to a substantially tubular expandable device known to one skilled in the art as a stent. Further, herein the terms "jacket", "stent jacket", "cover" and "stent cover" are often used interchangeably to refer to a substantially tubular stent jacket. Further, herein the terms "stent" and "stent assembly" are often used interchangeably to refer to a substantially tubular expandable device known to one skilled in the art as a stent associated with a jacket. From the context in which a given term is used, one skilled in the art is able to understand what is intended. In case of confusion, the reader is directed either to U.S. patent application Ser. No. 09/156,034 issued as U.S. Pat. No. 6,254,627 or to U.S. patent application Ser. No. 08/935,784 issued as U.S. Pat. No. 6,468,300 for clarification.

As shown in FIG. 1, a stent assembly 10 of this invention generally comprises a tubular, expandable metallic framework forming the stent 12 positioned coaxially within a cylinder 14 of heterologous tissue. Preferably, metallic stent 12 extends about 1 mm beyond each end of cylinder 14 to prevent prolapse of the tissue into the lumen of the stent when it is expanded. Cylinder 14 may be secured to metallic framework 12 by any suitable means. For example, four radially spaced sutures 16 may be placed at each end of cylinder 14.

Cylinder 14 preferably comprises bovine pericardium, a material shown to resist suture line bleeding, require no pre-clotting, support endothelialization and have an excellent host-tissue response. Further, bovine pericardial tissue has an elasticity of up to about 30% which allows the tissue cylinder to conform to both the unexpanded and expanded configurations of the metallic framework with out adding a great deal of bulk which increases the profile on the balloon. Other heterologous tissue suitable in the practice of the invention includes porcine pericardium, equine pericardium, heterologous peritoneum, heterologous pleura, aortic leaflet and others. Useful heterologous tissue is relatively impenetrable, which prevents tissue build up and the migration of smooth muscle cells through the stent framework. A particularly preferred bovine pericardium has cross-linked collagen and is available from Bio Vascular. Bovine pericardium tissue is available in a thickness ranging from about 0.25 mm to about 0.75 mm, with an average of about 0.45 mm. Thicknesses of 0.45 mm and less are preferred, so long as the mechanical strength remains sufficient.

Metallic stent 12 may comprise any suitable conventional stent. For example, Micro Stent II, available from Arterial Vascular Engineering, and Multi-Link, available from Guidant, have proven useful. Other stents that may be used in the practice of this invention include the Palmaz-Shatz stent from Johnson and Johnson, the Gianturco stent from Cook Incorporated and other commercially available stents. Conventional balloon expandable stents are preferred, but, as previously mentioned, self-expanding stents formed from shape memory materials are also suitable.

The cylinder of heterologous tissue 14, may be formed by cutting a rectangle of tissue having a length about 2 mm shorter than the stent on which it is to be mounted and a width about equal to the circumference of the expanded stent. The two sides corresponding to the length of the stent then may be secured together, such as by sewing with 6-0 or 7-0 polypropylene sutures 18. Other means for securing the sides of the stent cover together include mechanical means such as staples, adhesive or chemical bonding and the like. It may be desirable to support the tissue while manipulating it. For example, a 9 French introducer dilator may be used to support a 3 mm diameter cylinder, an 11 French dilator for a 3.5 mm cylinder and a 12 French dilator for a 4 mm cylinder. The tissue should be kept wet at all times during manipulation. Additionally, radio-opaque markers, such as rings of gold or platinum, may be added to the outer layer of the tissue so that the integrity of the cylinder may be assured before deployment. The cylinder of heterologous tissue is configured to be mounted onto a stent and generally has a length of about 5 to about 80 mm, preferably about 10 to about 50 mm and a diameter of about 2 to about 6 mm preferably about 2.5 to about 5 mm.

The use of the covered stent system generally follows conventional procedures. In particular, a guidewire is back-loaded into a delivery catheter having the covered stent assembly 10 loaded over an inflatable balloon or on a self expanding stent delivery system. The catheter and guidewire are percutaneously introduced by means of a conventional Seldinger technique and a 9 or 10 French guiding catheter into the patient's arterial system. The guidewire is advanced out delivery catheter through the vasculature under fluoroscopic imaging until it crosses a stenotic region. Then the catheter is advanced over the guidewire until the stent 10 is positioned at the desired location within the stenotic region. Then, the balloon is inflated or the securing mechanism of the self expanding stent is released to expand metallic framework 12 and tissue cylinder 14, seating the assembly within the vessel. The balloon is then deflated and the catheter is removed, leaving the expanded stent assembly in place.

Also with reference to FIG. 1, stent assembly 10 comprises a tubular, expandable metallic framework forming the stent 12 with an exterior jacket 14 of heterologous tissue. In the embodiment illustrated in FIG. 1, metallic stent 12 extends about 1 mm beyond each end of jacket 14 to prevent prolapse of the tissue into the lumen of the stent when it is expanded. Jacket 14 may be secured to metallic framework 12 by any suitable means. For example, four radially spaced sutures 16 may be placed at each end of jacket 14.

Figure 3:
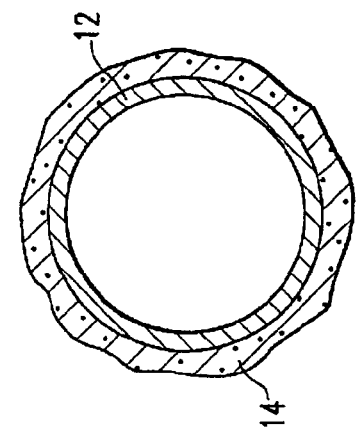
FIG. 3 is a transverse cross sectional view of the stent assembly shown in FIG. 1, taken along lines 3-3.

In a presently preferred embodiment of the stent assembly illustrated in FIG. 1, the jacket 14 contains a therapeutic or diagnostic agent, as shown in FIG. 3, illustrating a transverse cross section of the stent assembly shown in FIG. 1, taken along lines, 3-3.

Exterior jacket 14 preferably comprises bovine pericardium, a material shown to resist suture line bleeding, require no pre-clotting, support endothelialization and have an excellent host-tissue response. Further, bovine pericardial tissue has an elasticity of up to about 30% which allows the tissue cylinder to conform to both the unexpanded and expanded configurations of the stent 12 with out adding a great deal of bulk which increases the profile on the balloon. Other heterologous tissue suitable in the practice of the invention includes porcine pericardium, equine pericardium, heterologous peritoneum, heterologous pleura, aortic leaflet, veins and arteries, and others. Useful heterologous tissue is relatively impervious and impenetrable so as to prevent tissue build up and the migration of smooth muscle cells through the stent framework. A particularly preferred bovine pericardium has cross-linked collagen and is available from Bio Vascular. Bovine pericardium tissue is available in a thickness ranging from about 0.25 mm to about 0.75 mm, with an average of about 0.45 mm.

In a presently preferred embodiment of the invention, the biocompatible non-thrombogenic jacket 14 has a thickness of less than about 0.25 mm, and preferably has a thickness of about 0.05 mm to about 0.20 mm, and most preferably about 0.1 mm to about 0.15 mm. However, biocompatible non-thrombogenic jackets having a thickness of up to about 0.75 mm may be used. In the embodiment of the invention in which a thin biocompatible non-thrombogenic jacket having a thickness of less than about 0.25 mm is used, the heterologous tissue used to form the jacket is typically thinned before being assembled with the stent. The tissue may be thinned by a variety of suitable methods including peeling, shaving or otherwise removing a thin layer of the tissue. In a presently preferred embodiment, the thin jacket comprises the serous pericardium, which is the smooth, inner layer of the pericardium, which has been separated from at least a part of the outer layer of the pericardium. Similarly, where other forms of heterologous tissue are used, such as veins or arteries, the venous or arterial walls may be thinned to the presently preferred thickness of about 0.05 mm to about 0.20 mm. As a result of being thinned, the jacket may have reduced elasticity, so that the thin jacket is preferably provided on the unexpanded stent in a folded or overlapping wrapped configuration which provides sufficient material to cover the larger circumference of the expanded stent, as will be discussed in greater detail below.

Figure 4:
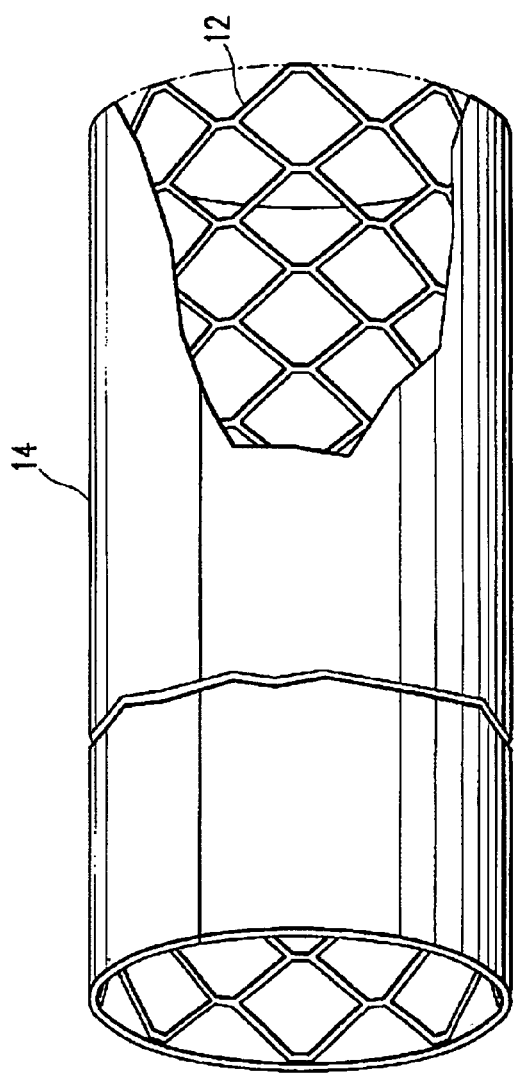
FIG. 4 is a perspective view, partially in section, of one embodiment of the stent assembly, shown in the expanded configuration, having a biocompatible non-thrombogenic jacket covering the length of the expandable stent.

The biocompatible non-thrombogenic jacket 14 preferably has a length configured to cover the length of the expanded stent, as illustrated in FIG. 4, showing an expanded stent 12 with a jacket 14 extending the length of the stent, with a length equal to the stent length. However, the jacket may have a length that is not equal to the length of the stent. For example, the jacket may have a length less than the stent length, as illustrated in FIG. 1, preferably not more than about 10%-20% less than the length of the stent. However, the jacket may cover an even smaller percentage of the length of the stent, as for example, when the stent assembly is used in a Transjugular Intrahepatic Portal Shunt (TIPS) application, where the jacket length is about 50% less than the length of the stent. Alternatively, the jacket may have a length greater than the length of the stent, preferably not more than about 5% greater than the stent length. The jacket preferably has a circumference about equal to the circumference of the expanded stent, configured to fit on an inner or outer surface of the expanded stent. The jacket preferably fits on the expanded stent so that the jacket conforms to the expanded stent without flaps of excess material.

Metallic stent 12 may comprise any suitable conventional stent. For example, Micro Stent II and GFX stents available from Arterial Vascular Engineering, and Multi-Link, available from Guidant, have proven useful. Other stents that may be used in the practice of this invention include the Palmaz-Shatz stent from Johnson and Johnson, the Gianturco stent from Cook Incorporated and other commercially available stents. Conventional balloon expandable stents are preferred, but, as previously mentioned, self-expanding stents, such as those formed from shape memory materials, are also suitable.

Figure 6:
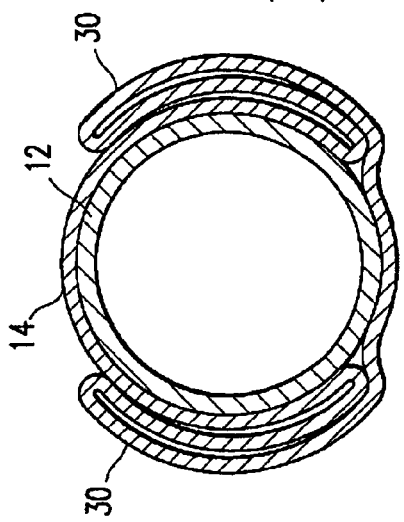
FIG. 6 is a transverse cross sectional view of another embodiment of the stent assembly prior to being expanded, illustrating the biocompatible non-thrombogenic jacket in a U-shaped folded configuration.
Figure 5:
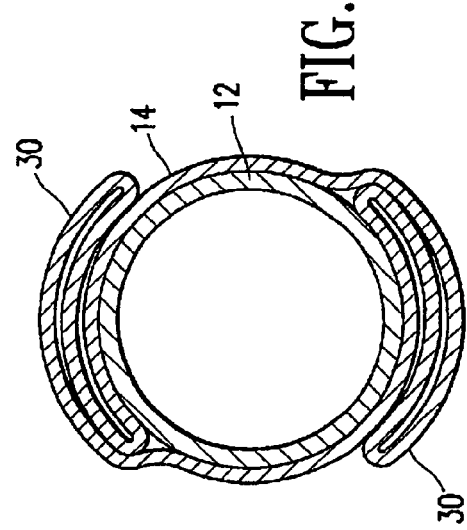
FIG. 5 is a transverse cross sectional view of one embodiment of the stent assembly prior to being expanded, illustrating the biocompatible non-thrombogenic jacket in a S-shaped folded configuration.

The stent assembly is formed by covering a surface of the unexpanded stent with the heterologous tissue forming the jacket 14. In one embodiment, the heterologous tissue is mounted onto the unexpanded stent in the form of a cylinder of tissue. The cylinder of heterologous tissue forming the jacket 14, may be formed by cutting a rectangle of tissue having a length about 2 mm shorter than the stent on which it is to be mounted and a width about equal to the circumference of the expanded stent. The two sides corresponding to the length of the stent then may be secured together, such as by sewing with 6-0, 7-0, 8-0 or 10-0 polypropylene sutures. Other means for securing the sides of the stent cover together include mechanical means such as staples, adhesive or chemical bonding and the like. It may be desirable to support the tissue while manipulating it. For example, a 9 French introducer dilator may be used to support a 3 mm diameter cylinder, an 11 French dilator for a 3.5 mm cylinder and a 12 French dilator for a 4 mm cylinder. The cylinder of tissue having a circumference about equal to the circumference of the expanded stent may be provided on the unexpanded stent in a folded or wrapped configuration. In one embodiment, the tissue on the unexpanded stent forms wings 30 on either side of the stent which are folded about stent, reducing the profile of the assembly, and unfolding upon expansion of the stent. In the embodiment illustrated in FIG. 5, the wings are folded in the same direction in an S-shaped configuration. In another embodiment, illustrated in FIG. 6, the wings of the cylinder of tissue on the unexpanded stent are folded about stent in opposite directions in a U-shaped configuration. However, the cylinder of tissue may be placed about the unexpanded stent in a variety of suitable configurations, as for example, where the wings of the cylinder of tissue are collapsed toward the stent, such as in an accordion type configuration (not shown). It would be apparent to one of skill in the art that the heterologous tissue forming the jacket could be folded about the unexpanded stent as outlined above whether or not the tissue had been formed into a cylinder of tissue before mounting onto the unexpanded stent.

In another embodiment, the heterologous tissue is wrapped around the unexpanded stent, so that sufficient tissue to cover the expanded stent is provided. In one embodiment, illustrated in FIG. 7, a ribbon of tissue is spirally wrapped around the unexpanded stent down a length thereof. The adjacent turns of the ribbon of tissue overlap, so that the ribbon unwraps as the stent expands to provide the jacket 14 configured to cover the expanded stent and having a circumference about equal to the circumference of the expanded stent. Preferably, the ribbon of tissue is wrapped along the entire length of the stent. In another embodiment, a rectangle of tissue having a width about equal to the circumference of the expanded stent on which it is to be mounted is repeatably wrapped around the outer circumference of the unexpanded stent, so that multiple layers of tissue are present on at least a part of the unexpanded stent, as shown in FIG. 8, illustrating a transverse cross section of an unexpanded stent with a wrapped jacket thereon. Preferably, one end of the tissue is fixed to the stent, and the tissue is then tightly wrapped around the stent. Upon expansion of the stent, the tissue unwraps to provide the jacket 14 having a circumference about equal to the circumference of the expanded stent. Preferably the length of the tissue is about equal to the length of the stent.

The tissue can be caused to remain in the folded or wrapped configurations until the stent is expanded by pressing the fluid out of the folded or wrapped tissue. Additionally, securing members such as surgical tape, ties, or breakable bands may be provided to releasably hold the tissue in the folded or wrapped configurations.

Depending upon the jacket material, the tissue may be kept wet at all times during manipulation or it may be dry until advanced into the patient's blood stream. Additionally, radio-opaque markers, such as rings of gold or platinum, may be added to the outer layer of the tissue so that the integrity of the cylinder may be assured before deployment within the body lumen. The cylinder of heterologous tissue configured to be mounted onto a stent and the jacket 14 formed by the cylinder of tissue or the unwrapped or unfolded tissue generally has a length, for coronary applications, of about 4 to greater than about 80 mm, typically about 5 to about 80 mm, preferably about 10 to about 50 mm, and a diameter of about 1.5 to about 35 mm, typically about 2 to about 6 mm, preferably about 2.5 to about 5 mm. The actual length and diameter of the cylinder of heterologous tissue may vary, and will depend on the nature of the vessel in which the stent assembly is implanted. For example, for peripheral vessel applications, such as an aortic abdominal aneurysm, a larger cylinder of heterologous tissue having a length of about 5 mm to about 200 mm and a diameter of about 2 mm to about 60 mm would be used.

Figure 2:
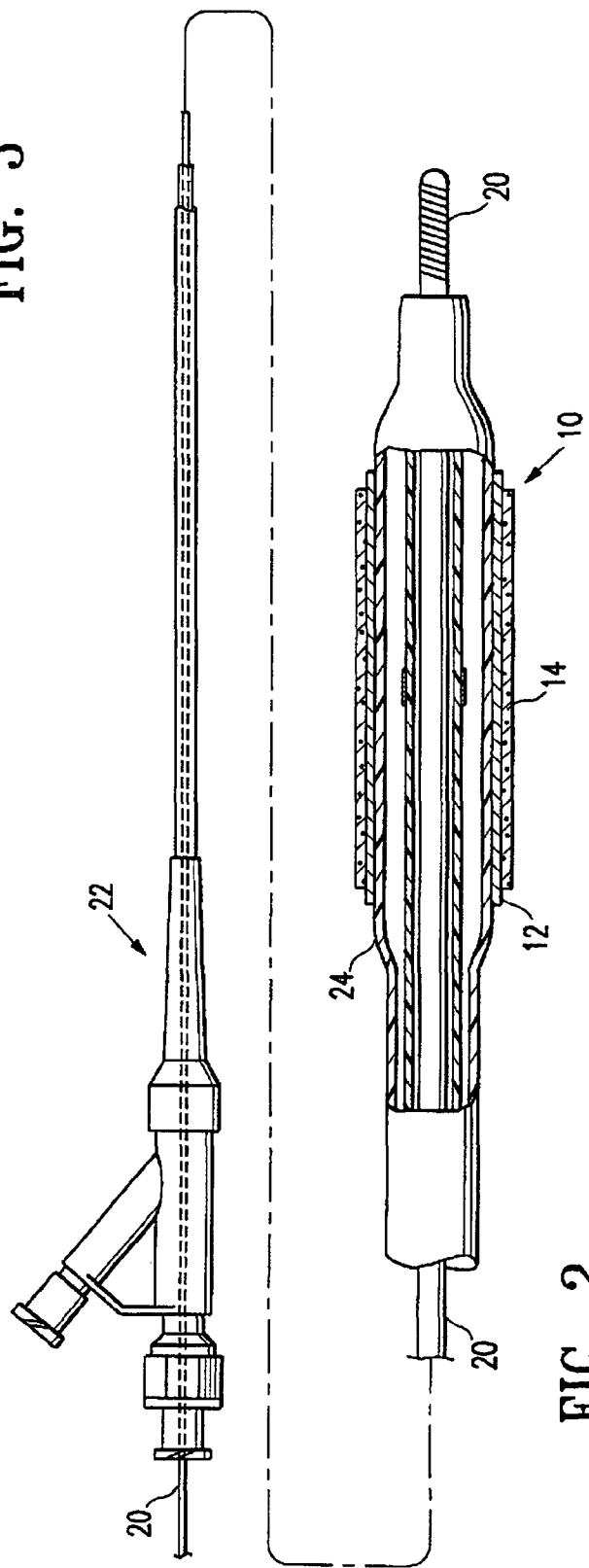
FIG. 2 is an elevational view, partially in section, of a delivery catheter having a jacketed stent mounted on an inflatable balloon on the distal extremity of the catheter.

The jacketed stent assembly 10 is inserted into the body lumen in the following fashion. A guidewire 20 is backloaded into a delivery catheter 22 having the jacketed stent assembly 10 mounted over an inflatable balloon 24 on the distal extremity of the delivery catheter (as schematically shown in FIG. 2) or on a self expanding stent delivery system (not shown). The catheter 22 and guidewire 20 are percutaneously introduced by means of a conventional Seldinger technique and a 5-9 or 10 French guiding catheter (not shown) into the patient's arterial system. Larger guiding catheters, for example up to about 25 French, may be used depending on the application. The guidewire 20 is advanced out delivery catheter 22 through the vasculature under fluoroscopic imaging until it crosses a stenotic region. Then the catheter 22 is advanced over the guidewire 20 until the stent assembly 10 is positioned at the desired location within the stenotic region. Then, the balloon 24 is inflated or the securing mechanism of the self-expanding stent is released to expand the stent 12 and cylindrical jacket 14, seating the assembly 10 within the vessel. The balloon 24 is then deflated and the catheter 22 is removed, leaving the expanded stent assembly 10 in place.

Although primarily described with respect to preventing restenosis in angioplasty patients, the covered stents of this invention may be used in a number of coronary artery, peripheral artery and non-vascular applications. For example, coronary artery applications include use in ectatic arteries and ectatic arteries containing an obstructive lesion, aneurismatic arteries, saphenous vein grafts and native arteries coronary perforation, coronary fistula, and ostial coronary lesions. Peripheral artery applications include aortic abdominal aneurysm and other aneurismatic peripheral arteries, transjugular intrahepatic portal shunt, percutaneous transluminal angioplasty, fistula closing and neuro interventions (such as aneurysms and arterial-venous malformations), small vessel intraluminal grafting, and ostial renal artery lesions. Finally, the covered stents of this invention may be used in urological, gastroenterological, respiratory, neurological, and other non-vascular applications. For example, urological field applications include urethral stenting for stenosis due to tumors, fibrous tissue and perforation. Gastroenterological field applications include fistula closing, reconstruction such as esophagus reconstruction, and esophageal bleeding. Respiratory field applications include tracheal and bronchial obstructions, and neurological field applications include carotid angioplasty.

A general description of the device of the present invention as well as a preferred embodiment of the present invention has been set forth above. One skilled in the art will recognize and be able to practice many changes in many aspects of the device described above, including variations that fall within the teachings of this invention. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims. The spirit and scope of the invention should be limited only as set forth in the claims which follow.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A stent assembly, comprising:
   a. an expandable stent shaped as a hollow cylinder; and
   b. functionally associated with said expandable stent, a stent jacket consisting of a smooth inner cell layer of a serous membrane and being devoid of a basement tissue fibrous layer, wherein the stent is positioned coaxially within the stent jacket.

2. The stent assembly of claim 1, wherein said jacket is fit about an outer surface of said expandable stent.

3. The stent assembly of claim 1, further comprising a therapeutic or diagnostic agent releasably contained within said stent jacket.

4. The stent assembly of claim 1, wherein the thinned serous membrane has a thickness of about 0.1 mm to about 0.15 mm.

5. The stent assembly of claim 1, wherein the stent jacket has a folded or overlapping wrapped configuration when applied to the stent.

6. A method of producing the stent assembly of claim 1, comprising:
   a. providing a sheet of serous membrane, the membrane including a smooth inner cell layer and an outer fibrous layer;
   b. thinning said sheet of serous membrane by removing the entirety of said outer fibrous layer thereby making a sheet of thinned serous membrane having a thickness of less than about 0.25 mm, wherein the thinned serous membrane comprises cells;
   c. associating said sheet of thinned serous membrane with an expandable stent shaped as a hollow cylinder, thereby producing the stent assembly, wherein the stent is positioned coaxially within the thinned serous membrane.

7. The method of claim 6, wherein said thinning is effected by at least one method selected from the group consisting of peeling and shaving.

8. The method of claim 6, wherein said associating includes wrapping said sheet about said expandable stent.

9. The method of claim 6, further comprising:
   d. impregnating said sheet of thinned serous membrane with a liquid containing a therapeutic or diagnostic agent.

* * * * *